US008987506B2

(12) United States Patent
Daugs

(10) Patent No.: US 8,987,506 B2
(45) Date of Patent: Mar. 24, 2015

(54) PROCESS FOR REDUCING INORGANICS FROM AND CONCENTRATING ANIONIC SURFACTANT SOLUTIONS

(75) Inventor: Edward D. Daugs, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 818 days.

(21) Appl. No.: 13/242,963

(22) Filed: Sep. 23, 2011

(65) Prior Publication Data

US 2012/0078008 A1    Mar. 29, 2012

Related U.S. Application Data

(60) Provisional application No. 61/386,726, filed on Sep. 27, 2010.

(51) Int. Cl.
*C07C 309/00* (2006.01)
*C07C 303/44* (2006.01)

(52) U.S. Cl.
CPC .................................. *C07C 303/44* (2013.01)
USPC ........................................................ 562/101

(58) Field of Classification Search
CPC ....................................................... C07C 303/44
USPC ............................................................. 562/101
See application file for complete search history.

(56) References Cited

U.S. PATENT DOCUMENTS 3,275,682 A * 9/1966 Bakker et al. ................. 562/111
2010/0179300 A1 * 7/2010 Boulos et al. ................. 528/310
2011/0015111 A1   1/2011 Yu et al.

FOREIGN PATENT DOCUMENTS

WO    WO 02055562 A2 *    7/2002

* cited by examiner

*Primary Examiner* — Sudhakar Katakam
*Assistant Examiner* — Kofi Adzamli

(57) ABSTRACT

A process including contacting one or more Strecker sulfonation reaction products of one or more halogenated alkyl ethers in the presence of sulfite with one or more polar water soluble organic solvents selected from acetone, methyl ethyl ketone, the $C_2$-$C_5$ alkyl alcohols, and the like, to form an extraction mixture; allowing the extraction mixture to separate into an aqueous phase and an organic phase; and separating the aqueous phase from the organic phase; wherein the one or more Strecker sulfonation reaction products each comprise at least 30 percent by weight of one or more inorganic salts and the organic phase following separation comprises less than 20 percent by weight of one or more inorganic salts, is provided.

14 Claims, 5 Drawing Sheets

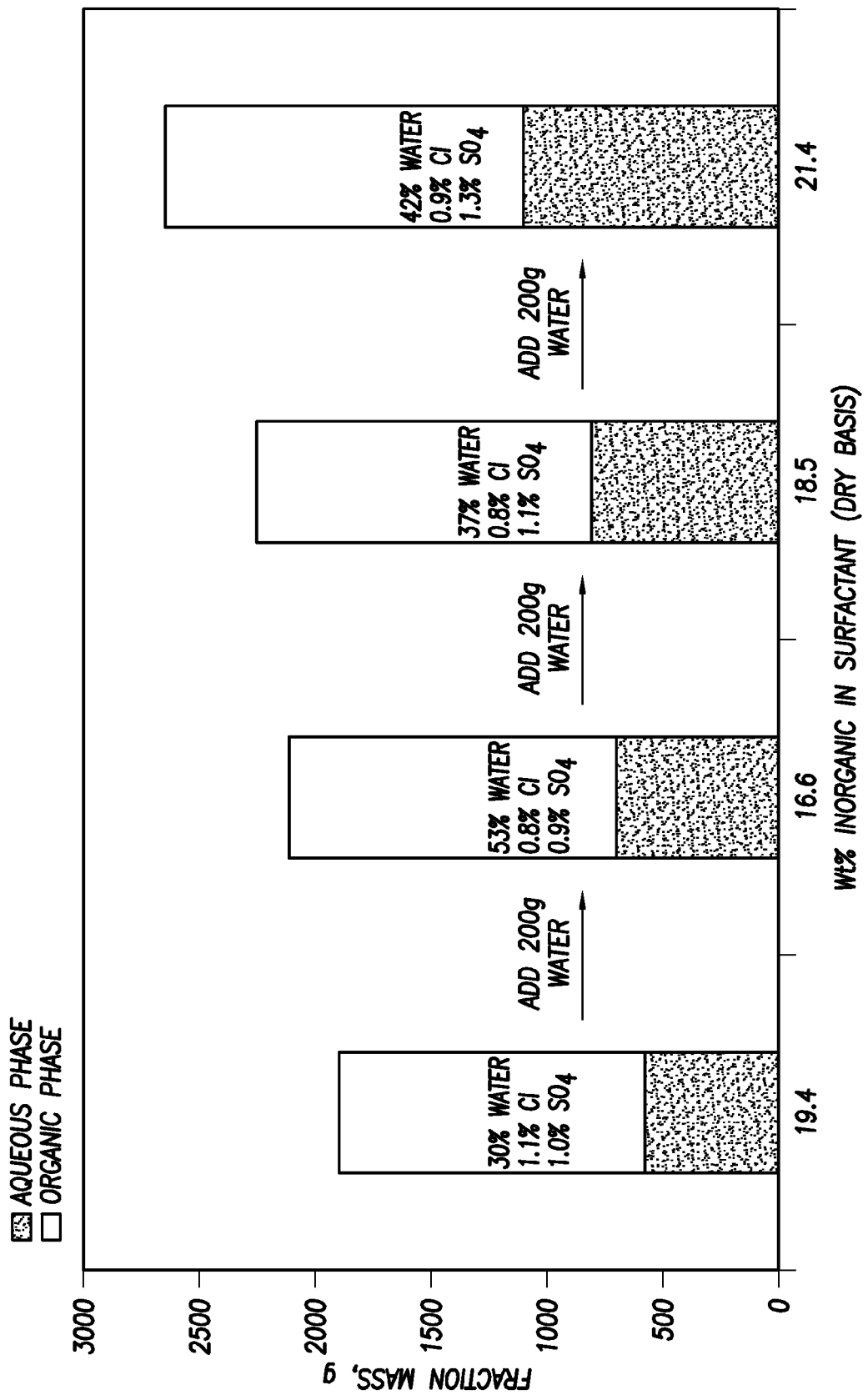

PROCESS FOR REDUCING INORGANICS FROM AND CONCENTRATING ANIONIC SURFACTANT SOLUTIONS

FIELD OF THE INVENTION

The invention relates to a process for removing inorganic salts from aqueous anionic surfactant solutions and for improving the surfactant concentration in such surfactant solutions. More particularly, the invention relates to a solvent extraction process and concentrative distillation for use with alkyl disulfonate surfactants.

BACKGROUND OF THE INVENTION

Anionic disulfonate surfactants may be prepared by Strecker sulfonation of alkyl di-chlorides with hydrophobic tail lengths of eight to sixteen carbons. Such surfactants contain excess inorganic salts as reaction by-products. The reaction may be generally described by equation (1) below:

$$RCl_2 + 2M_2SO_3 \rightarrow R(SO_3)_2M + MCl \quad (1)$$

where M is a metal such as Na, K, and R is an alkyl group having between eight and sixteen carbons.

Strecker sulfonation may also be used to sulfonate halogenated alkyl ethers. Halogenated alkyl ethers may be obtained from the acid catalyzed etherification of halogenated alkyl alcohols with α-olefins. For examples, mono- and di-sulfonate surfactants may be produced from Strecker sulfonation of alkyl ethers of 1,3-dichloro-2-propanol (DCP), as shown in equation (2):

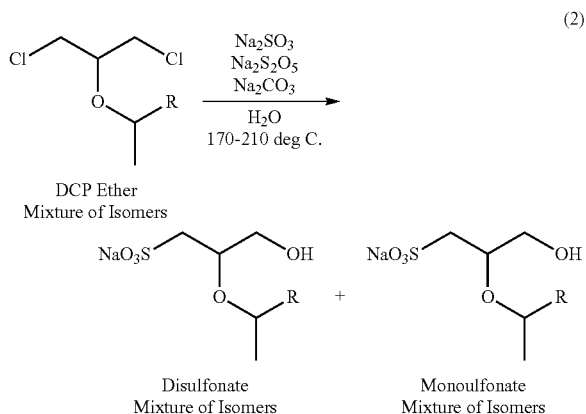

The reaction shown in equation (2) may be catalyzed by one or more metal halides, including for example sodium iodide. While equation (2) illustrates the DCP ether as being chlorinated, such Strecker sulfonation processes may be carried out with ethers having other halogen substituents, including for example, fluorine, iodine and bromine.

Inorganic salts are a by-product of such Strecker sulfonation processes. In fact, inorganic salts, typically sodium chloride, sodium sulfite and sodium sulfate, may constitute between 50 and 60% by weight of the sulfonation process product on a dry basis. Other reaction products of the Strecker process shown in equation (2) include non-polar organic species such as the unreacted halogenated alkyl ethers, alkyl alcohols from competitive hydrolysis, and long chain alkenes from dimerization of the α-olefin during etherification.

Such high levels of inorganic salts in surfactant solutions, however, may limit the use of the disulfonate surfactants in some applications such as emulsion polymerization, cleaning formulations, or personal care product formulations because inorganic salts may affect surfactant properties. Nevertheless, such disulfonate surfactants display other properties, such as biodegradability, hydrolytic and formulation stability, which are highly desirable.

Inorganic salts have been removed from anionic surfactant solutions by electrodialysis using a hydrophilic neutral membrane and a cation exchange membrane. Such removal process requires specialized processing equipment which significantly raises the cost of producing surfactants for applications where high inorganic salt levels cannot be tolerated. An additional drawback to using membrane technology for inorganic salt removal from anionic surfactant solutions is the generation of a large volume waste stream, typically four to six times the initial volume of the surfactant solution to be treated, containing low levels of surfactant product, along with the associated product loss. Consequently, a commercially facile and efficient method to remove or reduce the amount of residual inorganic salts in disulfonate alkyl surfactant solutions, particularly those arising from the sulfonation of halogenated alkyl ethers would be desirable. In addition to lowering the salt content of disulfonate surfactants, it is often desirable to produce aqueous concentrates of surfactants, especially because Strecker sulfonation process produces surfactant solutions having a relatively low surfactant concentration, i.e., ranging from 5 wt % to 20 wt % surfactant. Therefore, an economical and commercially practical process for concentrating the surfactant in disulfonate surfactant solutions would also be highly desirable.

SUMMARY OF THE INVENTION

The instant invention is a process for reducing or removing inorganic salts from Strecker sulfonation reaction products and a process for concentrating the surfactant component in Strecker sulfonation reaction products.

A first aspect of the invention provides a process comprising: contacting one or more Strecker sulfonation reaction products of one or more halogenated alkyl ethers in the presence of sodium sulfite with one or more polar water soluble organic solvents selected from acetone, methyl ethyl ketone, $C_2$-$C_5$ alkyl alcohols, and the like, to form an extraction mixture; allowing the extraction mixture to separate into an aqueous phase and an organic phase; and separating the aqueous phase from the organic phase; wherein the one or more Strecker sulfonation reaction products each comprise at least 30 percent by weight of one or more inorganic salts and the organic phase following separation comprises less than 18 percent by weight of one or more inorganic salts.

In some embodiments of the invention, the one or more halogenated alkyl ethers comprises one or more dihalogenated alkyl ethers.

In some embodiments of the process, the one or more dihalogenated alkyl ethers comprise one or more alkyl ethers of 1,3-dichloro-2-propanol wherein the alkyl group is selected from the group of alkyls having eight or more carbon atoms.

In some embodiments of the invention, the $C_2$-$C_5$ alkyl alcohols are selected from 1-propanol, 2-propanol and 1-butanol.

In some embodiments of the invention, the one or more inorganic salts are selected from, for example, sodium sulfite, sodium bisulfite, sodium bisulfate, sodium sulfate, sodium chloride, potassium sulfite, potassium bisulfite, potassium bisulfate, potassium sulfate, potassium chloride and combinations thereof, depending on the sulfite reagents chosen for use in the Strecker sulfonation reaction.

In some embodiments of the invention, the one or more Strecker sulfonation reaction products each comprise between 40 and 60 percent by weight of the one or more inorganic salts on a dry basis.

In some embodiments of the invention, the one or more Strecker sulfonation reaction products comprises between 25 and 60 percent by weight of the total weight of the one or more Strecker sulfonation products and the one or more water soluble organic solvents.

In some embodiments of the invention, the one or more Strecker sulfonation products and the organic phase following separation each comprise a surfactant component wherein the surfactant component of the organic phase is at least 75 percent by weight of the surfactant component of the one or more Strecker sulfonation products.

In some embodiments of the invention, the surfactant component of the organic phase and the surfactant component of the one or more Strecker sulfonation products each comprise one or more disulfonated alkyl ethers, one or more monosulfonated alkyl ethers, or a combination thereof.

A second aspect of the invention provides a process comprising: contacting one or more Strecker sulfonation reaction products of one or more halogenated alkyl ethers in the presence of sodium sulfite with one or more polar water soluble organic solvents selected from acetone, methyl ethyl ketone, $C_2$-$C_5$ alkyl alcohols, and the like, to form an extraction mixture; allowing the extraction mixture to separate into an aqueous phase and an organic phase; separating the aqueous phase from the organic phase; and distilling the organic phase under a stream of inert gas or other suitable means of distillation as to avoid foam generation to remove a portion of the one or more polar water soluble organic solvent and water there from and to obtain a concentrated surfactant solution, wherein the one or more Strecker sulfonation reaction products each comprise at least 30 percent by weight of one or more inorganic salts and the organic phase following separation comprises less than 18 percent by weight of one or more inorganic salts.

In some embodiments of the invention, the one or more halogenated alkyl ethers comprises one or more dihalogenated alkyl ethers.

In some embodiments of the invention, the concentrated surfactant solution comprises between 15 and 50 percent by weight of a surfactant component which comprises one or more disulfonated alkyl ethers, one or more monosulfonated alkyl ethers, or a combination thereof.

In some embodiments of the invention, the extraction mixture is further contacted with a non-polar organic solvent with low solubility selected from, for example, ethyl acetate, toluene, cyclohexane, diethyl ether, hydrocarbons, and the like, and combinations thereof.

In some embodiments of the invention, the non-polar organic solvent is present in an amount between 20 and 60 percent by weight of the total weight of the one or more water soluble organic solvents.

A third aspect of the invention provides a process comprising: adding sufficient peroxide to one or more Strecker sulfonation reaction products to achieve a positive peroxide test to form a peroxide/sulfonate mixture, thereby oxidizing residual sodium sulfite to sodium sulfate; contacting the peroxide-treated/sulfonate mixture with ethyl acetate to form a peroxide-treated/sulfonate/ethyl acetate mixture; allowing the peroxide-treated/sulfonate/ethyl acetate mixture to separate into an aqueous phase comprising the one or more Strecker sulfonation reaction products wherein undesired non-polar by-products have been removed there from; contacting the one or more Strecker sulfonation reaction products of one or more halogenated alkyl ethers in the presence of sodium sulfite with one or more polar water soluble organic solvents selected from, for example, acetone, methyl ethyl ketone, the $C_2$-$C_5$ alkyl alcohols, and the like to form an extraction mixture; allowing the extraction mixture to separate into an aqueous phase and an organic phase; and separating the aqueous phase from the organic phase; wherein the one or more Strecker sulfonation reaction products each comprise at least 30 percent by weight of one or more inorganic salts and the organic phase following separation comprises less than 18 percent by weight of one or more inorganic salts.

In some embodiments of the invention, the aqueous phase comprises no greater than 1 percent by weight of one or more surfactant components selected from the group of one or more disulfonated alkyl ethers, one or more monosulfonated alkyl ethers, and combinations thereof.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 5 illustrates the procedure for testing and the effect of excess water in 1-butanol extraction of a $C_{12}$ sulfonation reaction product.

DETAILED DESCRIPTION OF THE INVENTION

Figure 1:
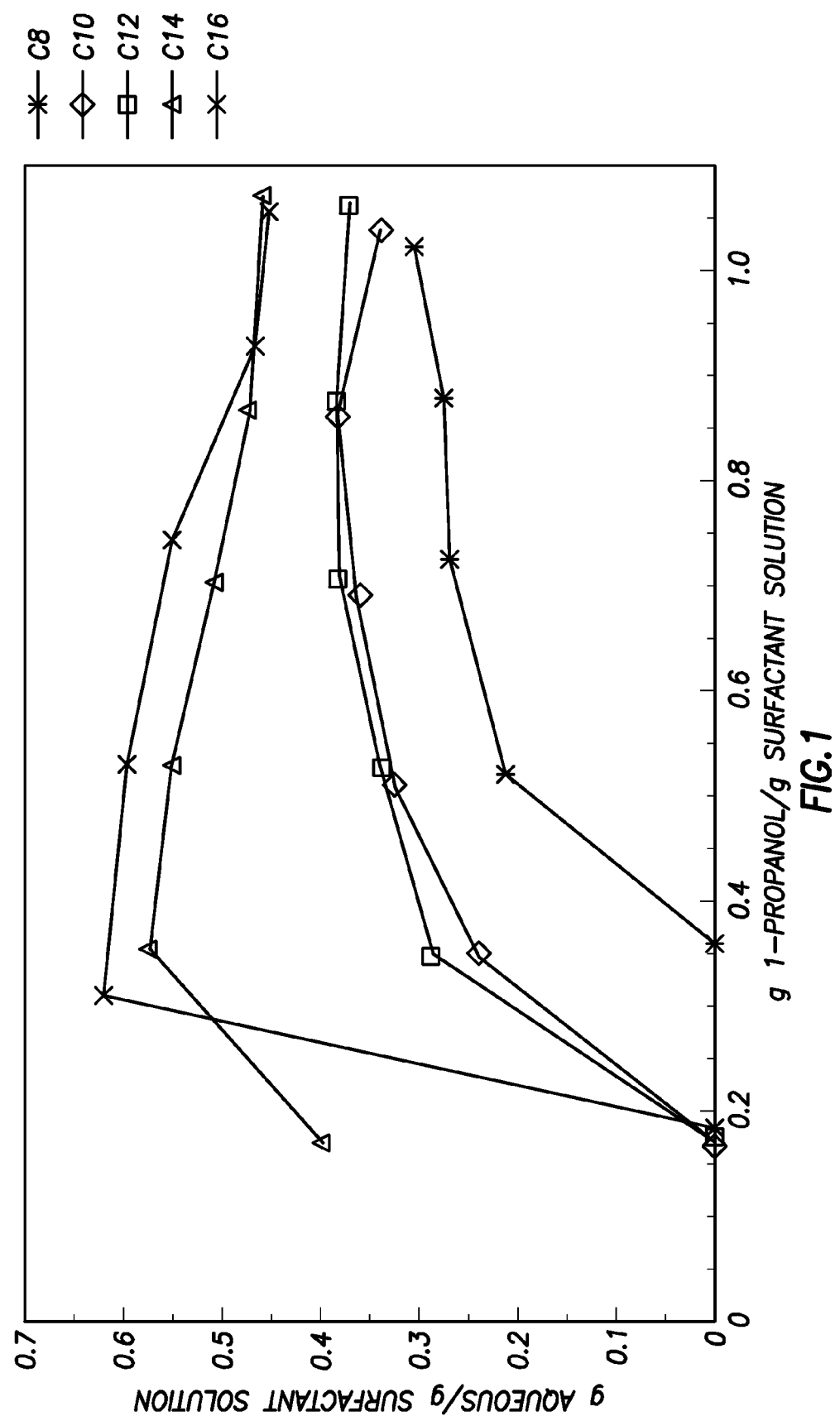
FIG. 1 compares the separated water phase weight with 1-propanol addition for several surfactant solutions and is a graph of gram of aqueous phase per gram surfactant vs. gram 1-propanol per gram of surfactant solution for each $C_8$, $C_{10}$, $C_{12}$, $C_{14}$ and $C_{16}$ surfactant solutions.
Figure 2:
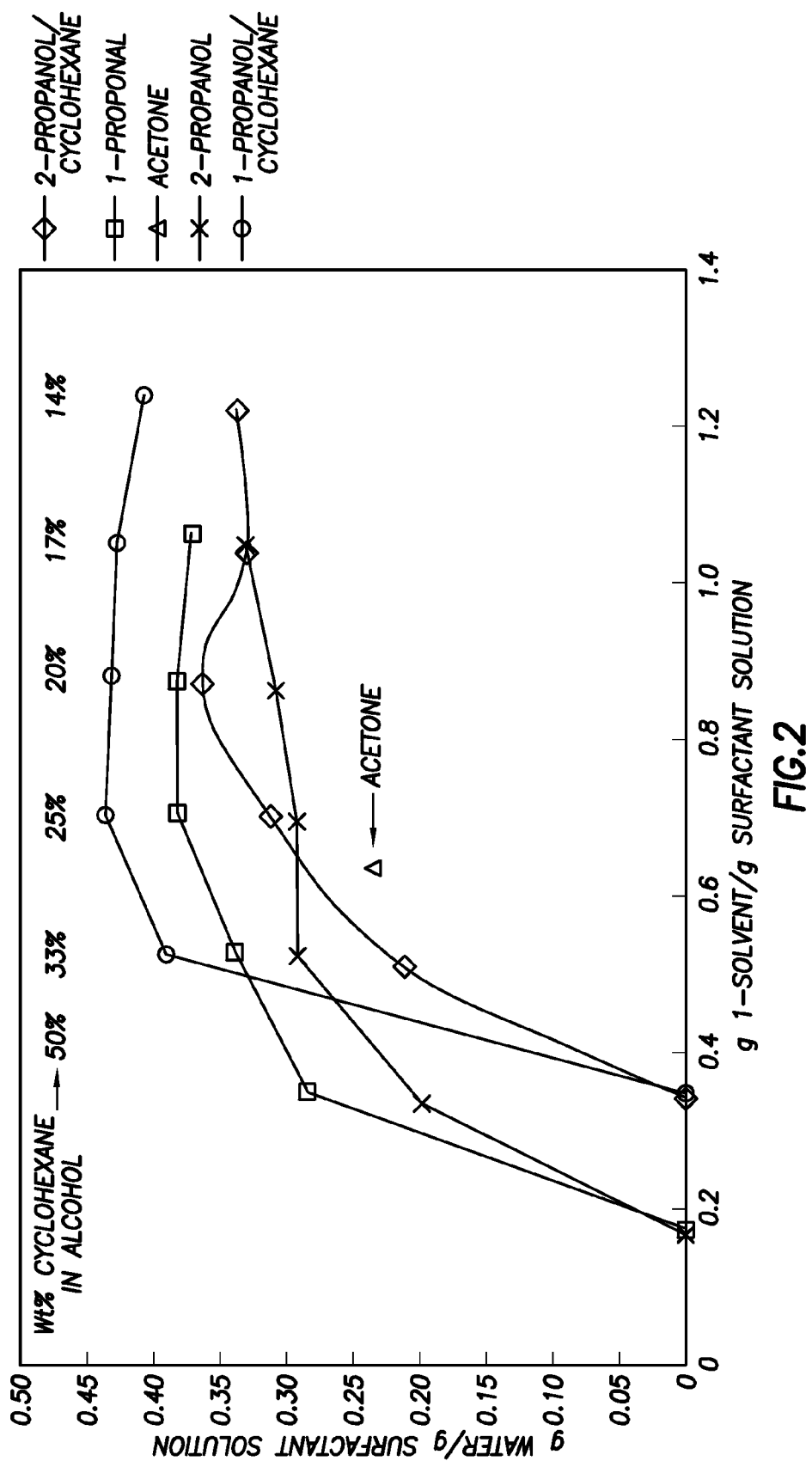
FIG. 2 illustrates the effect of alcohol charge on the amount of separated aqueous phase and is a graph of gram of water per gram of surfactant vs. gram alcohol solvent per gram of surfactant solution.
Figure 3:
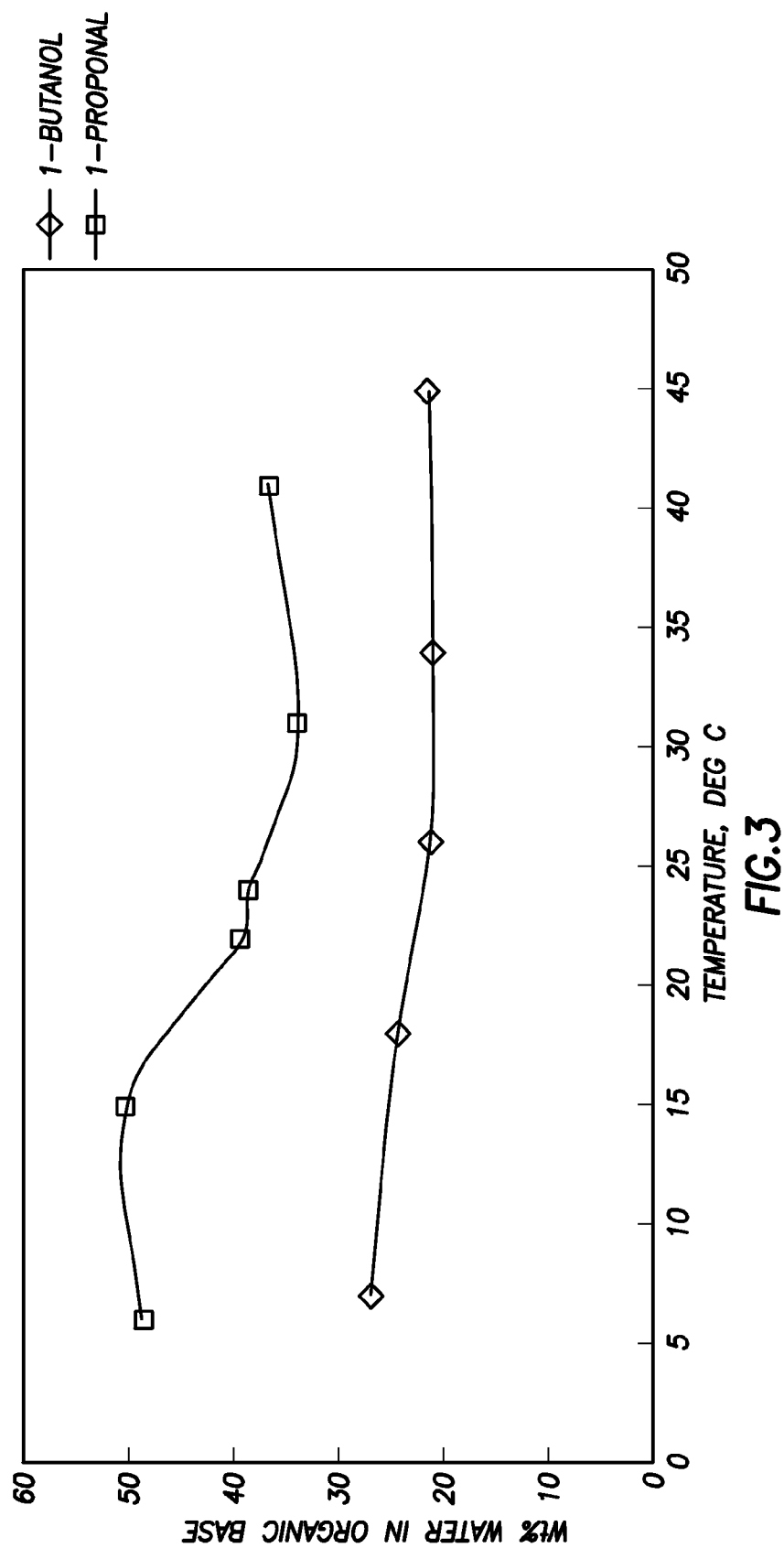
FIG. 3 illustrates the effect of temperature on the water content of a $C_{14}$ surfactant/alcohol phase and is a graph of weight % of water in the organic phase vs. temperature in °C.

The instant invention is a process for reducing or removing inorganic salts from Strecker sulfonation reaction products and a process for concentrating the surfactant component in Strecker sulfonation reaction products.

The process of the invention comprises: contacting one or more Strecker sulfonation reaction products of one or more halogenated alkyl ethers in the presence of sodium sulfite with one or more polar water soluble organic solvents selected from, for example, acetone methyl ethyl ketone, the $C_2$-$C_5$ alkyl alcohols, and the like, to form an extraction mixture; allowing the extraction mixture to separate into an aqueous phase and an organic phase; and separating the aqueous phase from the organic phase; wherein the one or more Strecker sulfonation reaction products each comprise at least 30 percent by weight of one or more inorganic salts and one or more surfactant components and the organic phase following separation comprises less than 18 percent by weight of the one or more inorganic salts.

The one or more Strecker sulfonation reaction products of one or more halogenated alkyl ethers in the presence of sodium sulfite may comprise one or more surfactant components selected from disulfonated alkyl ethers, monosulfonated alkyl ethers, and combinations thereof.

In some embodiments of the invention, the one or more halogenated alkyl ethers comprises one or more dihalogenated alkyl ethers.

The disulfonated alkyl ethers may include any surfactant having the general formula $(NaO_3S)_2R'OR$, where R' is an alkyl group having 3 or more carbon atoms and R is a linear or branched or mixture thereof alkyl group having 8 or more carbon atoms. R' may be, in some embodiments, a propyl, butyl, pentyl or hexyl group. R may be, in some embodiments, an alkyl group having between 8 and 16 carbon atoms.

The monosulfonated alkyl ethers may include any surfactant having the general formula $(NaO_3S)(OH)R'OR$, where R' is an alkyl group having 3 or more carbon atoms and R is a linear or branched or mixture thereof alkyl group having 8 or more carbon atoms. R' may be, in some embodiments, a propyl, butyl, pentyl or hexyl group. R may be, in some embodiments, an alkyl group having between 8 and 16 carbon atoms.

The starting feedstock for the Strecker sulfonation reaction may be selected from any mono- or dihalogenated alkyl ethers having the general formula $XnR'OCR$, where n may be 1 or 2, X is a halogen, is an alkyl group having 3 or more carbon atoms and R is a linear or branched or mixture thereof alkyl group having 8 or more carbon atoms. In preferred embodiments, starting feedstock is a mixture of isomers of the alkyl ethers of 1,3-dichloro-2-propanol. In certain specific embodiments, the one or more dihalogenated alkyl ethers comprise one or more alkyl ethers of 1,3-dichloro-2-propanol wherein the alkyl group has eight or more carbon atoms.

The one or more Strecker sulfonation reaction products each comprise at least 30 percent by weight of one or more inorganic salts on a dry basis. The one or more inorganic salts may be selected from the group of sodium sulfite, sodium bisulfite, sodium bisulfate, sodium sulfate, sodium chloride, and the potassium counter parts, and combinations thereof. In one aspect, the sulfite and bisulfite species may be oxidized to sulfate and bisulfate by addition of, for example, hydrogen peroxide. All individual values and subranges at least 30 percent by weight are included herein and disclosed herein; for example, the percent by weight of the one or more inorganic salts in the one or more Strecker sulfonation reaction products may be from a lower limit of 30, 35, 40, 45, or 50 weight percent to an upper limit of 35, 40, 45, 50, 55, or 60 weight percent on a dry basis. For example, the percent by weight of the one or more inorganic salts in the one or more Strecker sulfonation reaction products from 30 to 60 weight percent, or in the alternative, from 40 to 50 weight percent, or in the alternative, from 40 to 60 weight percent, or in the alternative from 50 to 60 weight percent.

The one or more polar water soluble organic solvents may be one or more of any polar organic solvent that has good solubility of the one or more Strecker sulfonation reaction products. In preferred embodiments, the water soluble organic solvents also have boiling points sufficiently low to allow for removal by distillation under conditions which do not negatively impact the surfactant components of the Strecker sulfonation reaction products.

The one or more polar water soluble organic solvents, in some embodiments, are selected from the group of acetone, methyl ethyl ketone, the $C_2$-$C_5$ alkyl alcohols, and the like. In preferred embodiments, the polar water soluble organic solvents are miscible with water in all concentrations, but yet unexpectedly yield a surfactant-containing organic phase when added to the Strecker sulfonation reaction products which readily separates from an aqueous phase containing very low levels (for example, less than 0.1 wt %) of the anionic surfactant products. Table 1 provides selected physical properties of preferred polar water soluble organic solvents useful in the inventive process.

TABLE 1

| | Density g/cc | b.p. ° C. | Water Solubility | Water Azeotrope b.p. ° C. | % Water in Azeotrope |
|---|---|---|---|---|---|
| Acetone | 0.788 | 57 | Miscible | Nonazeotrope | — |
| 2-Propanol | 0.781 | 82 | Miscible | 80.3 | 12.6 |
| 1-Propanol | 0.802 | 97 | Miscible | 87 | 28.3 |
| 1-Butanol | 0.810 | 118 | 9.1 mL/100 mL @ 25° C. | 93 | 42.4 |

The contacting of the one or more Strecker sulfonation reaction products with the one or more polar water soluble organic solvents may be accomplished using any equipment or procedure allowing for mixing of liquids. For example, the contacting may be accomplished in a tank equipped with a mechanical or electromagnetic stirrer, paddle or similar mechanism. Alternatively, the one or more Strecker sulfonation reaction products may be contacted with the one or more water soluble organic solvents by turbulent flow through piping or during loading into a vessel. The contacting of the one or more Strecker sulfonation reaction products with the one or more water soluble organic solvents may be accomplished batch wise or in a continuous fashion, wherein a stream of the Strecker sulfonation reaction products is mixed with the one or more water soluble organic solvents in a mixing zone and transferred to a second settling zone in which phase separation occurs.

The contacting of the one or more Strecker sulfonation reaction products with the one or more polar water soluble organic solvents may occur at any temperature equal to or greater than 10° C. All individual values and subranges from greater than 10° C. are included herein and disclosed herein; for example, the temperature during contacting may be from a lower limit of 10, 15, 20, 25 or 30° C. to an upper limit of 25, 30, 35, 40, 50, or 60° C. For example, the temperature during contacting may be from 10 to 60° C., or in the alternative, from 20 to 50° C., or in the alternative, from 30 to 50° C., or in the alternative from 35 to 55° C.

The contacting of the one or more Strecker sulfonation reaction products with the one or more polar water soluble organic solvents may occur for a period greater than one minute. All individual values and subranges from greater than one minute are included herein and disclosed herein; for example, the contacting time may be from a lower limit of 1, 5, 7, 10, 15, 20, 25 or 30 minutes to an upper limit of 5, 10, 15, 20, 30, 40 or 60 minutes. For example, the contacting time may be from 1 to 60 minutes, or in the alternative, from 5 to 15 minutes, or in the alternative, from 10 to 30 minutes, or in the alternative from 20 to 40 minutes.

The allowing of the extraction mixture to form into an aqueous phase and an organic phase may occur using any appropriate equipment and procedure, including for example, by allowing the extraction mixture to sit unagitated in a tank or similar vessel. Alternatively, the formation of the two phases may be aided through the use of any appropriate equipment or procedure known to those skilled in the art, including for example, subjecting the extraction mixture to centrifugal forces in a cyclone.

The aqueous and organic phases may be separated using any appropriate equipment and procedure, including for example, decanting the organic phase from the aqueous phase. Alternatively, the phase may be separated by siphoning the aqueous phase from a vessel containing the two phases. The phase separation operation may be conducted batchwise or in a continuous fashion, wherein a mixture of the two phases is introduced to a settling zone and each separated phase collected from the upper and lower sections of the settling zone.

The organic phase following separation comprises less than 20 percent by weight of the one or more inorganic salts. All individual values and subranges of less than 20 percent by weight are included herein and disclosed herein; for example, the percent by weight of the one or more inorganic salts in the organic phase may be from a lower limit of 0, 5, 10, or 15 weight percent to an upper limit of 5, 10, 15, or 20 weight percent. For example, the percent by weight of the one or more inorganic salts in the organic phase from 0 to 20 weight percent, or in the alternative, from 5 to 15 weight percent, or in the alternative, from 10 to 15 weight percent, or in the alternative from 10 to 20 weight percent.

The extraction mixture comprises between 5 and 60 percent by weight of the one or more Strecker sulfonation reaction products. All individual values and subranges between 5 and 60 percent by weight are included herein and disclosed herein; for example, the percent by weight of the one or more Strecker sulfonation reaction products in the extraction mixture may be from a lower limit of 5, 15, 25, 45, or 55 weight percent to an upper limit of 10, 20, 50, or 60 weight percent. For example, the percent by weight of the one or more Strecker sulfonation reaction products in the extraction mixture may be from 5 to 60 weight percent, or in the alternative, from 30 to 50 weight percent, or in the alternative, from 30 to 40 weight percent, or in the alternative from 35 to 45 weight percent.

The organic phase following separation comprises one or more surfactant components, the total amount of which is at least 75 percent of the amount of the one or more surfactant components of the one or more Strecker sulfonation products. All individual values and subranges of at least 75 percent of the amount of the one or more surfactant components of the one or more Strecker sulfonation products are included herein and disclosed herein; for example, the total amount of the one or more surfactant components in the organic phase may be from a lower limit of 75, 80, 85, 90, or 95 percent of the amount of the one or more surfactant components of the one or more Strecker sulfonation products to an upper limit of 80, 85, 90, 95, or 100 percent of the amount of the one or more surfactant components of the one or more Strecker sulfonation products.

In some embodiments, the process further comprises distilling the organic phase under a stream of nitrogen or other inert gas to remove a portion of the one or more water soluble organic solvents and a portion of the water there from and to obtain a concentrated surfactant solution. The concentrated surfactant solution may comprise between 15 and 50 percent by weight of one or more surfactant components. All individual values and subranges between 15 and 50 percent by weight are included herein and disclosed herein; for example, the percent by weight of the one or more surfactant components in the concentrated surfactant solution may be from a lower limit of 15, 20, 30, 40, or 50 weight percent to an upper limit of 20, 30, 40, or 50 weight percent. For example, the percent by weight of the one or more surfactant components in the concentrated surfactant solution may be from 15 to 50 weight percent, or in the alternative, from 20 to 40 weight percent, or in the alternative, from 30 to 40 weight percent, or in the alternative from 35 to 45 weight percent, or in the alternative from 40 to 50 weight percent. Alternative distillation procedures that avoid foam generation from the surfactant solution, such as use of wiped film or rolled film distillation equipment, may also be used.

The nitrogen (or any inert gas) sweeps over the near-boiling surfactant solution allowing evaporation of solvent and concentration of the solution without foam formation, which would carry the surfactant solution into the distillation receiver. Equipment such as a rolled or wiped film distillation apparatus may alternatively be used in other embodiments of the invention.

The polar water soluble organic solvent may be recovered from the distillate for recycle and reuse.

In some embodiments of the inventive process, the extraction mixture may be further contacted with an non-polar organic solvent having low solubility in water, for example ethyl acetate, cyclohexane, toluene, ethyl ether, alkanes, haloalkanes, and the like, and combinations thereof. The non-polar organic solvent is typically in an amount of from 20 to 60 percent by weight of the extraction mixture. All individual values and subranges between 20 and 60 percent by weight are included herein and disclosed herein; for example, the percent by weight of the one or more organic solvents may be from a lower limit of 20, 30, 40, 50, or 55 weight percent to an upper limit of 25, 30, 40, 50, or 60 weight percent, based on the total weight of the one extraction mixture. For example, the percent by weight of the one or more organic solvents in the extraction mixture may be from 20 to 60 weight percent, or in the alternative, from 30 to 50 weight percent, or in the alternative, from 30 to 40 weight percent, or in the alternative from 35 to 45 weight percent, based on the total weight of the extraction mixture.

In some embodiments, the inventive process further comprises adding sufficient peroxide, generally to a slight excess, to the one or more Strecker sulfonation reaction products, either before or following the salt removal process, to achieve a positive peroxide test to oxidize sulfite species to sulfate species and form a peroxide-treated/sulfonate mixture; contacting the peroxide-treated/sulfonate mixture with ethyl acetate to form a peroxide-treated/sulfonate/ethyl acetate mixture; allowing the peroxide-treated/sulfonate/ethyl acetate mixture to separate into a water soluble surfactant phase comprising the one or more Strecker sulfonation reaction products wherein undesired non-polar by-products have been removed there from, prior to contacting the Strecker sulfonation reaction product mixture with the one or more polar water soluble organic solvents. The separating of the peroxide-treated/sulfonate/ethyl acetate mixture may occur using any of the equipment and procedures discussed previously.

In some embodiments of the invention, the aqueous phase comprises no greater than 1 percent by weight of the one or more surfactant components. All individual values and subranges of less than 1 percent by weight are included herein and disclosed herein; for example, the percent by weight of the one or more surfactant components in the aqueous phase may be from a lower limit of 0, 0.25, 0.3, 0.4, 0.5, 0.6, 0.7, 0.8 or 0.9 weight percent to an upper limit of 0.25, 0.3, 0.4, 0.5, 0.7, 0.8, 0.9 or 1 weight percent. For example, the percent by weight of the one or more surfactant components in the aqueous phase may be from 0 to 1 weight percent, or in the alternative, from 0.3 to 0.5 weight percent, or in the alternative, from 0.5 to 0.8 weight percent, or in the alternative from 0.75 to 1 weight percent.

In some embodiments of the invention, the organic solvent/surfactant solution may be clarified by filtration to remove particulate matter. This filtration operation may be performed prior to, during, or after the distillation operation in which the polar organic solvent is removed and the concentration of the surfactant is increased.

EXAMPLES

The following examples illustrate the present invention but are not intended to limit the scope of the invention. The examples of the instant invention demonstrate that substantial reduction of the inorganic salt content of a sulfonation reaction solution while maintaining efficient recovery of the surfactant may be achieved in accordance with the present invention. The examples of the instant invention further demonstrate that the concentration of the surfactant in the reduced inorganic salt organic phase may be readily achieved.

As used in the examples below, the term $C_X$ sulfonate reaction product means the reaction product of Equation (2), where X represents the number of carbons in R, an alkyl group. As discussed above, the CR sulfonate reaction product includes both disulfonate and monosulfonate products as well as a variety of by-products. The percent by weight of each of the disulfonate and monosulfonate components are given for each $C_X$ sulfonate reaction product, as analyzed by high pressure liquid chromatography.

Inventive Example 1

1-Butanol Extraction of $C_{12}$ Sulfonate Reaction Product

A 1 liter (L) reparatory funnel was charged with 646.2 g of $C_{12}$ sulfonate reaction product (9.6 wt % $C_{12}$ Disulfonate, 5.2 wt % $C_{12}$ Monosulfonate) and 516.4 g of 1-butanol. The mixture was shaken, then allowed to settle to give a clean phase separation. The bottom aqueous phase (311.2 g) showed less than 0.1 wt % of $C_{12}$ sulfonates by HPLC analysis. The top organic phase (841.7 g) was loaded to the 1 L surfactant concentration equipment described below under Test Methods, and concentrated. A total of 800 g of water was added using the addition funnel and removed by evaporation to a final temperature in the 1 L vessel of 104° C., giving a white emulsion in the 1 L vessel weighing 160 g. Upon standing, the white emulsion formed a clear yellow liquid. HPLC analysis of the solution found 30.7 wt % of $C_{12}$ Disulfonate (49 g, 79% recovery) and 15.8 wt % of $C_{12}$ Monosulfonate (25 g, 75% recovery).

Inventive Example 2

Water Rejection from Sulfonate Reaction Product Solutions with Solvent Addition

A number of 20 milliliter (mL) glass vials were charged with 4.00 mL of a $C_{12}$ surfactant reaction product (11.1 wt % $C_{12}$ Disulfonate, 6.3 wt % $C_{12}$ Monosulfonate) and 1 to 6 mLs of either 1-propanol or 2-propanol, the solutions were mixed, and then allowed to stand undisturbed to give clean phase separations. The lower separated aqueous phase was removed using a glass pipet to a separate vial and weighed. To each separated alcohol phase was added 1.00 mL of cyclohexane or ethyl acetate, the solutions were mixed, and then allowed to stand undisturbed to give clean phase separations. When formed, the lower separated aqueous phase was removed using a glass pipet to a separate vial and weighed. Similar extractions using $C_8$ surfactant reaction product (16.5 wt % $C_8$ Disulfonate, 3.5 wt % $C_8$ Monosulfonate), $C_{10}$ surfactant reaction product (14.5 wt % $C_{10}$ Disulfonate, 4.9 wt % $C_{10}$ Monosulfonate), $C_{14}$ reaction product (5.4 wt % $C_{14}$ Disulfonate, 3.6 wt % $C_{14}$ Monosulfonate), and $C_{16}$ surfactant reaction product (3.2 wt % $C_{16}$ Disulfonate, 3.7 wt % $C_{16}$ Monosulfonate) surfactant solutions in lieu of the $C_{12}$ surfactant reaction product are summarized in Table 2.

TABLE 2

| Sulfonate Reaction Product | Dilution Solvent | g Solvent/g Reaction Solution | g Aqueous/g Reaction Solution |
|---|---|---|---|
| $C_8$ | 2-Propanol | 0.86 | 0.28 |
|  | 1-Propanol | 1.0 | 0.30 |
|  | 22% EtOAc in 1-Propanol | 0.92 | 0.32 |
| $C_{10}$ | 2-Propanol | 0.86 | 0.32 |
|  | 1-Propanol | 0.86 | 0.38 |
| $C_{12}$ | 2-Propanol | 0.86 | 0.30 |
|  | 20% Cyclohexane in 2-Propanol | 0.87 | 0.36 |
|  | 1-Propanol | 0.71 | 0.38 |
|  | 25% Cyclohexane in 1-Propanol | 0.71 | 0.44 |
| $C_{14}$ | 2-Propanol | 0.50 | 0.44 |
|  | 1-Propanol | 0.36 | 0.57 |
|  | 33% Cyclohexane in 1-Propanol | 0.54 | 0.60 |
| $C_{16}$ | 2-Propanol | 0.53 | 0.44 |
|  | 54% EtOAc in 2-Propanol | 0.36 | 0.73 |
|  | 1-Propanol | 0.32 | 0.62 |
|  | 37% EtOAc in 1-Propanol | 0.51 | 0.71 |

Inventive Examples 3 and 4

Effect of Extraction Temperature on Water Content

A 100 mL jacketed bottom-drain glass reactor was charged with 57.2 g of an ethyl acetate-washed $C_{14}$ reaction product (4.2 wt % $C_{14}$ disulfonate, 3.1 wt % $C_{14}$ monosulfonate) and 24.4 g of 1-butanol—Inventive Example 3. The jacket temperature was controlled using a Lauda RM20 recirculating heating and cooling bath. The two phase mixture was stirred using an overhead stirrer for 30 minutes at a constant internal temperature of 18° C. (jacket temperature 15° C.), the stirrer stopped, and a 1 g sample removed for Karl Fisher analysis. The temperature was subsequently adjusted to a number of different temperatures, as shown in Table 3, held at that temperature for 30 minutes and a 1 g sample removed for Karl Fisher analysis. Inventive Example 4—55.0 g of $C_{14}$ reaction product and 29.2 g of 1-propanol—was similarly prepared, subjected to various temperatures and analyzed at each temperature. Table 3 summarizes the results.

TABLE 3

| Inventive Example 3 | | | |
|---|---|---|---|
| 1-Butanol | Jacket Temp ° C. | Internal Temp ° C. | Wt % Water in Organic Phase |
| 1 | 15 | 18 | 24.2 |
| 2 | 3 | 7 | 26.8 |
| 3 | 28 | 26 | 21.1 |
| 4 | 38 | 34 | 20.8 |
| 5 | 50 | 45 | 21.3 |
| Inventive Example 4 | | | |
| 1-Propanol | Jacket Temp ° C. | Internal Temp ° C. | Wt % Water in Organic Phase |
| 1 | 24 | 24 | 38.3 |
| 2 | 1 | 6 | 48.4 |

TABLE 3-continued

| 3 | 13 | 15 | 50.0 |
| 4 | 24 | 22 | 39.1 |
| 5 | 37 | 31 | 33.6 |
| 6 | 44 | 41 | 36.5 |

Increased water rejection from the organic phase increases the level of inorganic salt rejection from the water phase. That is, improved phase separation between aqueous and organic phases improves the removal of inorganic salts from the organic phase, and therefore, from the resultant surfactant solution. As is seen in Table 14, temperature appeared to have less effect on the 1-butanol extraction than on the 1-propanol extraction. For 1-propanol extraction, a phase separation temperature of 30 to 35° C. gave the least amount of water in the organic phase. For 1-butanol extraction, a phase separation temperature of 35 to 40° C. gave the least amount of water in the organic phase.

Inventive Examples 5 and 6

Effect of Excess Water in Inorganic Salt Extraction

Figure 4:
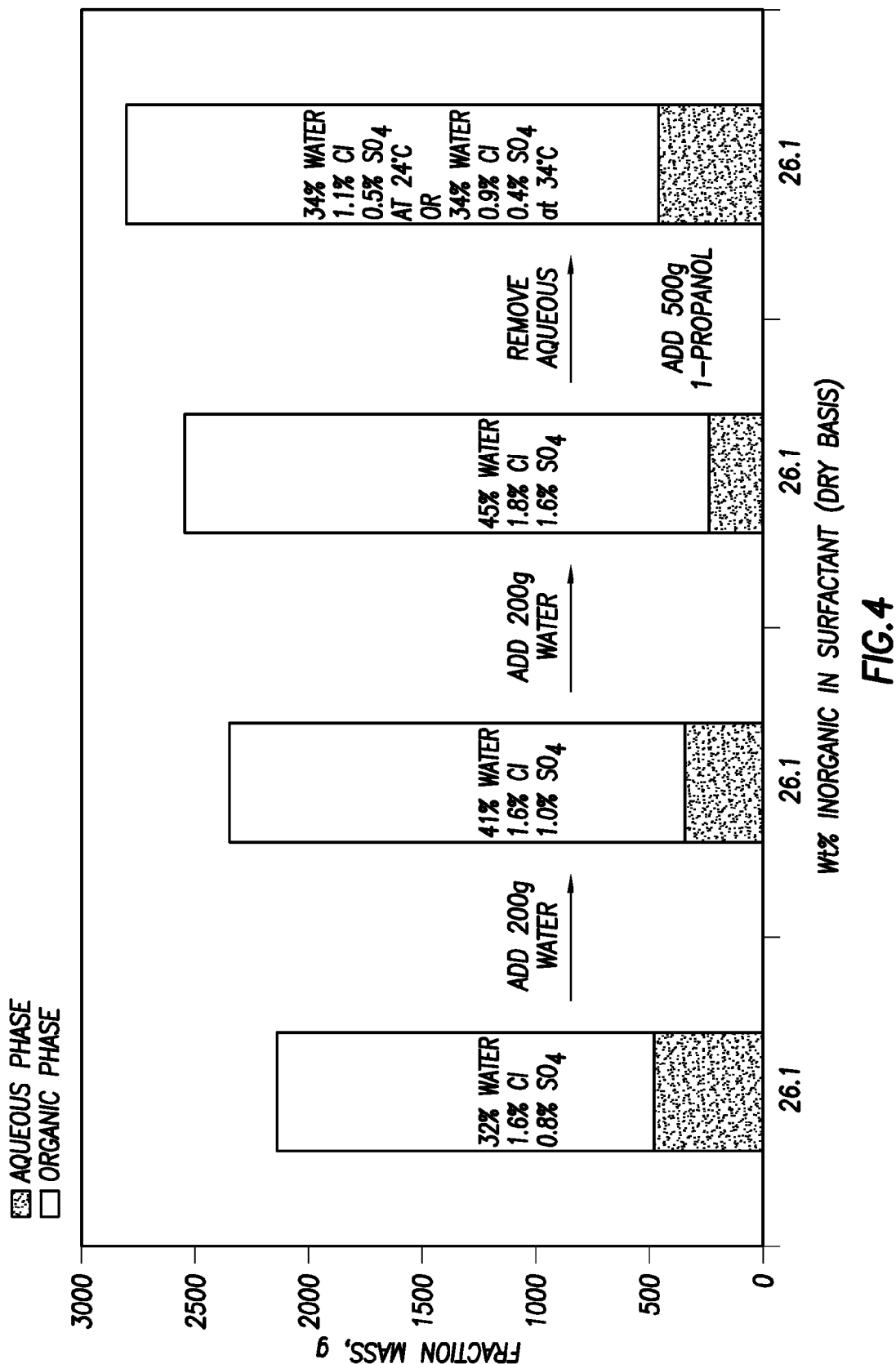
FIG. 4 illustrates the procedure for testing and the effect of excess water in a 1-propanol extraction on $C_{12}$ sulfonation reaction product.

Inventive Example 5 was prepared as follows:

A 5 liter (L) jacketed bottom-drain glass reactor with an overhead stirrer was charged with 1317.9 g of $C_{12}$ sulfonate reaction product (8.0 wt % $C_{12}$ Disulfonate and 5.0 wt % $C_{12}$ Monosulfonate). With cold water flowing through the jacket system, a total of 71 mL of 30% hydrogen peroxide was added to a positive peroxide test (QUANTOFIX™ Peroxide 100 Test Sticks available from Macherey-Nagel GmbH & Co., Düren, Germany). The mixture was diluted with 665.3 g of ethyl acetate, stirred for 8 minutes, and the stirrer turned off to allow the phases to settle. After 45 minutes, the bottom aqueous phase (1478.8 g) was removed and retained. The ethyl acetate phase (568.3 g) was removed and evaporated to a residue of 21.70 g. The residue was discarded. The aqueous phase was charged to the reactor and diluted with 650.8 g of 1-propanol with stirring. After stirring for 15 minutes, the stirrer was turned off and the phases allowed to settle for 45 minutes. The lower aqueous phase (480 g) was removed. Analysis of the organic phase found that it contained 32.7 wt % water, 1.62 wt % chloride, and 0.81 wt % sulfate. The 480 g aqueous phase and 200 g of water was recharged to the 5 L vessel. After stirring for 5 minutes, the stirrer was turned off and the phases allowed to settle for 45 minutes. The lower aqueous phase (344.1 g) was removed. Analysis of the organic phase found that it contained 40.6 wt % water, 1.57 wt % chloride, and 1.00 wt % sulfate. The 344.1 g aqueous phase and 200 g of water was recharged to the 5 L vessel. After stirring for 5 minutes, the stirrer was turned off and the phases allowed to settle for 55 minutes. The lower aqueous phase (227.8 g) was removed. Analysis of the organic phase found that it contained 45.4 wt % water, 1.75 wt % chloride, and 1.57 wt % sulfate. The 227.8 g aqueous phase was discarded, and the organic phase was charged with 500 g of 2-propanol. After stirring for 1 minute, the phases were allowed to settle for 10 minutes at 24° C. Analysis of the organic phase found that it contained 33.6 wt % water, 1.09 wt % chloride, and 0.48 wt % sulfate. The internal temperature was increased to 34° C. and held constant using a West Controller-controlled steam valve on the water jacket system. The lower aqueous phase (433.6 g) was drained and discarded. Analysis of the 2319.7 g organic phase found that it contained 34.4 wt % water, 0.94 wt % chloride, and 0.42 wt % sulfate. The organic phase was vacuum filtered through filter paper to remove a solid precipitate. Analysis of the filtrate found that it contained 0.98 wt % chloride and 0.26 wt % sulfate. The filtered solution was charged to the 2 L distillation system and heated to distil under a nitrogen purge. A total of 500 mL of additional water was added and removed during the distillation. The final clear yellow concentrate (471.1 g) contained 18.9 wt % $C_{12}$ Disulfonate (85% recovery), 10.9 wt % $C_{12}$ Monosulfonate (78% recovery), 4.54 wt % chloride, and 1.60 wt % sulfate. FIG. 4 illustrates the results of this testing.

Inventive Example 6 was prepared and treated in the exact same manner as Inventive Example 5 except that 1-butanol was used in lieu of 1-propanol. FIG. 5 illustrates the results for Inventive Example 6.

FIGS. 4 and 5 plot the weights of the upper organic and lower aqueous phases found after the addition of the alcohol to the ethyl acetate-washed $C_{12}$ reaction product, and the weights after successive addition of 200 g charges of fresh water. Included in FIGS. 5 and 6 are the chloride, sulfate, and water concentrations found in the upper organic phases, and the corresponding wt % of inorganic salts in the surfactant (on a dry basis).

As can be seen in FIG. 4, in Inventive Example 5, with each water addition, the level of water in the organic phase increased, the size of the separated aqueous phase decreased, and the residual inorganic content in the organic phase and the surfactant product increased. After the second 200 g water addition, the aqueous phase was removed and the organic phase was diluted with an additional 500 g of 1-propanol, generating a second aqueous phase and reduced the residual inorganic content of the organic phase. Slightly more water and inorganic salts were rejected from the organic phase when the temperature was increased from 24 to 34° C.

As can be seen in FIG. 5, in Inventive Example 6, each water addition increased the size of the aqueous phase. The minimum size organic phase (1345 g) was found before the water additions; it increased by about 50 g after the first water addition, 50 g after the second, and by 100 g after the third water addition. The minimum inorganic content in the organic phase and the surfactant product was found after the first water addition. Product was isolated from the 1-butanol solution after the third water addition. The residual inorganic content of the product isolated in this trial was slightly higher than the two other 1-butanol trials that did not include addition of 600 g of excess water.

The following examples illustrate both the reduction/removal of inorganic salts by extraction and the concentration of the surfactant by distillation. The distillation system utilized in the following examples was as follows:

A 2 L round bottom flask was placed into a West controller-controlled heating mantle and fit with a thermocouple, overhead stirrer, addition funnel, and distillation head with an Allihn condenser to a 1 L distillation receiver. A flow of nitrogen was supplied over the solution in the distillation vessel and exiting through the distillation head condenser and receiver. The nitrogen flow and temperature setpoint were adjusted to control foam generation during the extraction solvent distillation.

Inventive Examples 7-11

Salt Removal and Concentration for $C_{10}$ Sulfonate Reaction Product

Inventive Example 7 was prepared as follows:

A 5 L jacketed bottom-drain glass reactor with an overhead stirrer was charged with 1228.6 g of $C_{10}$ sulfonate reaction product (13.0 wt % $C_{10}$ Disulfonate and 4.5 wt % $C_{10}$ Monosulfonate). With cold water flowing through the jacket system, a total of 60 mL of 30% hydrogen peroxide was added to a positive peroxide test (QUANTOFIX™ Peroxide 100 Test Sticks). The mixture was diluted with 608.7 g of ethyl acetate, stirred for 30 minutes, and the stirrer turned off to allow the phases to settle. The bottom aqueous phase (1368.8 g) was removed and retained. The ethyl acetate phase (532.2 g) was removed and evaporated to a residue of 28.05 g. The residue, containing primarily polar byproducts such as decanol and unreacted ether, was discarded. The aqueous phase was charged to the reactor and diluted with 866.5 g of 1-propanol with stirring. After stirring for 30 minutes, the stirrer was turned off and the phases allowed to settle. The lower aqueous phase (475.8 g) was removed and discarded. The upper organic phase (1759.1 g) was vacuum filtered through filter paper, then charged to the 2 L distillation system described above and heated to distil under a nitrogen purge. A total of 200 mL of additional water was added and removed during the distillation. The final clear yellow concentrate (589.3 g) contained 25.6 wt % $C_{10}$ Disulfonate (95% recovery by weight), 9.4 wt % $C_{10}$ Monosulfonate (100% recovery by weight), 3.20 wt % chloride, and 1.86 wt % sulfate.

Table 4 sets out the foregoing information for Inventive Example 7 as well as for Inventive Examples 8-11 which were similarly prepared and treated, except as specifically noted in Table 4.

$C_{12}$Monosulfonate). With cold water flowing through the jacket system, a total of 65 mL of 30% hydrogen peroxide was added to a positive peroxide test (QUANTOFIX® Peroxide 100 Test Sticks). The mixture was diluted with 669 g of ethyl acetate, stirred for 5 minutes, and the stirrer turned off to allow the phases to settle. After 35 minutes, the bottom aqueous phase (1479.7 g) was removed and retained. The ethyl acetate phase (566.0 g) was removed and evaporated to a residue of 22.95 g. The residue was discarded. The aqueous phase was charged to the reactor and diluted with 327.7 g of 1-propanol with stirring. The internal temperature was increased to 32° C. and held constant using a West Controller-controlled steam valve on the water jacket system. After stirring for 20 minutes, the stirrer was turned off and the phases allowed to settle for 35 minutes. The lower aqueous phase (481.5 g) was removed and discarded. An additional 336.5 g of 1-propanol was added. No additional phase separation was noted. The upper organic phase (1568.5 g) was vacuum filtered through filter paper, then charged to the 2 L distillation system described above and heated to distil under a nitrogen purge. A total of 400 mL of additional water was added and removed during the distillation. The final clear yellow concentrate (418.6 g) contained 20.7 wt % $C_{12}$-Disulfonate (87% recovery by weight), 12.0 wt % $C_{12}$ Monosulfonate (82% recovery by weight), 4.11 wt % chloride, and 1.48 wt % sulfate.

TABLE 4

|  | Extraction Solvent | Wt % Di/Mono Feed | Wt % Di/Mono Concentrate | Wt % Cl/SO$_4$ Concentrate | Wt % Inorganics (Solution) | Wt % Inorganics (Dry Basis) |
| --- | --- | --- | --- | --- | --- | --- |
| Inventive Example 7 | 1-Propanol | 13.0/4.5 | 25.6/9.4 | 3.20/1.86 | 8.04 | 18.7 |
| Inventive Example 8 | 2-Propanol* | 13.0/4.6 | 25.4/8.8 | 5.60/2.10 | 12.34 | 26.5 |
| Inventive Example 9 | 1-Propanol† | 11.5/3.9 | 22.5/7.5 | 3.46/1.53 | 7.97 | 21.0 |
| Inventive Example 10 | 1-Propanol† | 10.3/3.8 | 22.7/8.3 | 3.50/1.72 | 8.31 | 21.1 |
| Inventive Example 11 | 1-Butanol | 11.9/4.4 | 36.6/12.5 | 3.90/2.30 | 9.83 | 16.7 |

*Hydrogen peroxide added to alcoholic surfactant solution
†Aqueous phase separation performed at 30 to 35° C.

Inventive Examples 12

Salt Removal and Concentration for $C_{12}$Sulfonation Reaction Product

Inventive Example 12 was prepared as follows:

A 5 L jacketed bottom-drain glass reactor with an overhead stirrer was charged with 1326.7 g of $C_{12}$sulfonate reaction product (7.5 wt % $C_{12}$-Disulfonate and 4.6 wt %

Table 5 summarizes the foregoing information for Inventive Example 12 as well as for Inventive Examples 13-22 which were similarly prepared and treated, except as specifically noted in Table 5.

TABLE 5

|  | Extraction Solvent | Wt % Di/Mono Feed | Wt % Di/Mono Concentrate | Wt % Cl/SO$_4$ Concentrate | Wt % Inorganics (Solution) | Wt % Inorganics (Dry Basis) |
| --- | --- | --- | --- | --- | --- | --- |
| Inventive Example 12 | 1-Propanol† | 7.5/4.6 | 20.7/12.0 | 4.11/1.48 | 8.97 | 21.5 |
| Inventive Example 13 | 2-Propanol | 8.5/5.0 | 21.8/11.9 | 6.80/1.50 | 13.43 | 28.5 |
| Inventive Example 14 | 1-Propanol* | 10.9/5.9 | 23.5/12.2 | 3.00/1.76 | 7.63 | 17.6 |
| Inventive Example 15 | 1-Propanol* | 7.9/4.7 | 22.5/12.6 | 3.20/1.20 | 7.05 | 16.7 |
| Inventive Example 16 | 1-Propanol | 7.5/4.6 | 24.9/14.6 | 3.90/2.50 | 10.13 | 20.4 |
| Inventive Example 17 | 1-Propanol | 8.1/4.7 | 21.9/11.9 | 2.88/0.90 | 6.08 | 15.2 |
| Inventive Example 18 | 1-Propanol | 8.1/4.9 | 18.5/10.5 | 2.82/1.14 | 6.34 | 17.9 |

TABLE 5-continued

| | Extraction Solvent | Wt % Di/Mono Feed | Wt % Di/Mono Concentrate | Wt % Cl/SO$_4$ Concentrate | Wt % Inorganics (Solution) | Wt % Inorganics (Dry Basis) |
|---|---|---|---|---|---|---|
| Inventive Example 19 | 1-Propanol† | 6.8/4.4 | 19.8/11.7 | 3.55/3.68 | 11.30 | 26.4 |
| Inventive Example 20 | 1-Butanol* | 8.6/4.6 | 30.0/15.0 | 2.20/1.90 | 6.44 | 12.5 |
| Inventive Example 21 | 1-Butanol | 8.1/4.7 | 20.9/11.5 | 1.98/1.65 | 5.71 | 15.0 |
| Inventive Example 22 | 1-Butanol | 8.2/5.1 | 20.4/12.0 | 4.11/1.48 | 8.97 | 21.5 |

*Hydrogen peroxide added to alcoholic surfactant solution
†Aqueous phase separation performed at 30 to 35° C.

Inventive Examples 23-29

Salt Removal and Concentration for $C_{14}$Sulfonation Reaction Product

Inventive Example 23 was prepared and treated as follows:
A 5 L jacketed bottom-drain glass reactor with an overhead stirrer was charged with 1361.6 g of $C_{14}$sulfonate reaction product (4.1 wt % $C_{14}$ Disulfonate and 3.1 wt % $C_{14}$Monosulfonate). With cold water flowing through the jacket system, a total of 89 mL of 30% hydrogen peroxide was added to a positive peroxide test (QUANTOFIX™ Peroxide 100 Test Sticks). The mixture was diluted with 674 g of ethyl acetate, stirred for 5 minutes, and the stirrer turned off to allow the phases to settle. After 30 minutes, the bottom aqueous phase (1474.8 g) was removed and retained. The ethyl acetate phase (642.9 g) was removed and evaporated to a residue of 75.33 g. The residue was discarded. The aqueous phase was charged to the reactor and diluted with 613 g of 1-propanol with stirring. The internal temperature was increased to 35° C. and held constant using a West Controller-controlled steam valve on the water jacket system. After stirring for 10 minutes, the stirrer was turned off and the phases allowed to settle for 25 minutes. The lower aqueous phase (775.7 g) was removed and discarded. The upper organic phase (1278.7 g) was vacuum filtered through filter paper, then charged to the 2 L distillation system described above and heated to distil under a nitrogen purge. A total of 600 mL of additional water was added and removed during the distillation. The final clear yellow concentrate (465.0 g) contained 11.0 wt % $C_{14}$-Disulfonate (92% recovery by weight), 8.1 wt % $C_{14}$ Monosulfonate (89% recovery by weight), 1.57 wt % chloride, and 1.36 wt % sulfate.

Table 6 sets out the foregoing information for Inventive Example 23 as well as for Inventive Examples 24-29 which were similarly prepared and treated, except as specifically noted in Table 6.

TABLE 6

| | Extraction Solvent | Wt % Di/Mono Feed | Wt % Di/Mono Concentrate | Wt % Cl/SO$_4$ Concentrate | Wt % Inorganics (Solution) | Wt % Inorganics (Dry Basis) |
|---|---|---|---|---|---|---|
| Inventive Example 23 | 1-Propanol† | 4.1/3.1 | 11.0/8.1 | 1.56/1.36 | 4.58 | 19.4 |
| Inventive Example 24 | 2-Propanol | 5.1/3.8 | 12.0/8.6 | 4.40/1.00 | 8.73 | 29.8 |
| Inventive Example 25 | 1-Propanol* | 7.5/5.9 | 16.3/13.3 | 2.60/1.86 | 7.04 | 19.2 |
| Inventive Example 26 | 1-Propanol | 5.3/4.0 | 19.9/14.7 | 2.40/1.40 | 6.03 | 14.8 |
| Inventive Example 27 | 1-Propanol† | 4.2/3.0 | 13.7/9.4 | 2.07/1.88 | 3.73 | 21.1 |
| Inventive Example 28 | 1-Butanol* | 5.7/4.3 | 16.0/12.4 | 1.80/1.70 | 5.48 | 16.2 |
| Inventive Example 29 | 1-Butanol | 4.2/3.1 | 13.3/9.9 | 0.59/1.01 | 2.47 | 9.6 |

*Hydrogen peroxide added to alcoholic surfactant solution
†Aqueous phase separation performed at 30 to 35° C.

Inventive Examples 30-34

Salt Removal and Concentration for $C_{16}$ Sulfonation Reaction Product

Inventive Example 30 was prepared and treated as follows:
A 5 L jacketed bottom-drain glass reactor with an overhead stirrer was charged with 1264.7 g of a mixture of two $C_{16}$ sulfonate reaction products (637.5 g of a first $C_{16}$ sulfonate reaction product, 2.4 wt % $C_{16}$ Disulfonate and 3.1 wt % $C_{16}$ Monosulfonate and 627.2 g of a second $C_{16}$ sulfonate reaction product, 2.1 wt % $C_{16}$ Disulfonate and 2.5 wt % $C_{16}$ Monosulfonate). With cold water flowing through the jacket system, a total of 49 mL of 30% hydrogen peroxide was added to a positive peroxide test (QUANTOFIX™ Peroxide 100 Test Sticks). The mixture was diluted with 595 g of ethyl acetate, stirred for 5 minutes, and the stirrer turned off to allow the phases to settle. After 30 minutes, the bottom aqueous phase (1363.4 g) was removed and retained. The ethyl acetate phase (529.7 g) was removed and evaporated to a residue of 29.11 g. The residue was discarded. The aqueous phase was charged to the reactor and diluted with 507 g of 1-butanol with stirring.

The internal temperature was increased to 35° C. and held constant using a West Controller-controlled steam valve on the water jacket system. After stirring for 8 minutes, the stirrer was turned off and the phases allowed to settle for 40 minutes. The lower aqueous phase (897.3 g) was removed and discarded. The upper organic phase (956.7 g) was vacuum filtered through filter paper, then charged to the 2 L distillation system described above and heated to distil under a nitrogen purge. A total of 900 mL of additional water was added and removed during the distillation. The final clear yellow concentrate (359.4 g) contained 9.4 wt % $C_{16}$ Disulfonate, 11.4 wt % $C_{16}$ Monosulfonate, 0.62 wt % chloride, and 0.65 wt % sulfate.

Table sets out the foregoing information for Inventive Example 30 as well as for Inventive Examples 31-34 which were similarly prepared and treated, except as specifically noted in Table 7.

TABLE 8

|  | Gradient | RT (min) Disulfonate | RT (min) Monosulfonate |
|---|---|---|---|
| $C_8$ | 100% A (3 min) to 100% B at 30 min | 7.5 min | 13.1 min |
| $C_{10}$ | 100% A (0 min) to 100% B at 22 min | 6.5 min | 10.3 min |
| $C_{12}$ | 90% A (0 min) to 100% B at 22 min | 6.8 min | 11.8 min |
| $C_{14}$ | 80% A (0 min) to 100% B at 20 min | 6.3 min | 11.0 min |
| $C_{16}$ | 80% A (0 min) to 100% B at 20 min | 8.5 min | 13.8 min |

Ion Chromatography Analysis

Ion chromatography analysis for determining chloride and sulfate concentrations was carried out on a DIONEX DX-120 ion chromatograph (available from DIONEX CORPORATION) by injecting a 25 μL sample onto a 4×250 mm IonPac AS22 column and eluting at 1.2 mL/min with 4.0 mM sodium

TABLE 7

|  | Extraction Solvent | Wt % Di/Mono Feed | Wt % Di/Mono Concentrate | Wt % Cl/SO$_4$ Concentrate | Wt % Inorganics (Solution) | Wt % Inorganics (Dry Basis) |
|---|---|---|---|---|---|---|
| Inventive Example 30 | 1-Butanol† | 2.2/2.8 | 9.4/11.4 | 0.62/0.65 | 1.98 | 8.7 |
| Inventive Example 31 | 2-Propanol* | 3.3/4.2 | 8.2/9.6 | 2.60/1.20 | 6.06 | 25.4 |
| Inventive Example 31 | 1-Propanol | 3.2/4.0 | 10.6/12.7 | 1.60/1.50 | 4.86 | 17.2 |
| Inventive Example 32 | 1-Butanol | 3.2/4.1 | 10.8/12.8 | 0.65/0.64 | 2.02 | 7.9 |
| Inventive Example 33 | 1-Butanol† | 2.4/2.7 | 8.2/9.5 | 0.73/0.86 | 2.47 | 12.2 |
| Inventive Example 34 | 1-Butanol† | 2.2/2.8 | 9.4/11.4 | 0.62/0.65 | 1.98 | 8.7 |

*Hydrogen peroxide added to alcoholic surfactant solution
†Aqueous phase separation performed at 30 to 35° C.

TEST METHODS

DCP Sulfonate solutions were prepared according to the process disclosed in U.S. patent application Ser. No. 12/827,165, filed Jun. 30, 2010 and having a priority date of Jul. 16, 2009, the disclosure of which is incorporated herein by reference.

High Pressure Liquid Chromatography

High pressure liquid chromatography (HPLC) analysis for determining DCP-based surfactant concentrations was carried out on an ChemStation controlled Agilent 1100 HPLC system by injecting 20 μL of sample onto a 150 mm×4.6 mm ALTIMA $C_{18}$ 5 micron column at 40° C. and eluting at 1 mL/min with the solvent gradient of A (90/10 water/acetonitrile, 0.01 M ammonium acetate) and B (10/90 water/acetonitrile, 0.01 M ammonium acetate) listed in Table 8. Run time was 30 minutes. Detection was using an Alltech 2000 Evaporative Light Scattering Detector with a drift tube temperature of 75° C. and a 2.2 mL/min nitrogen flow, or an ESA Corona plus corona discharge detector operating at 35 psi nitrogen, 30° C. The detector response curve, which was quadratic, was calibrated using standard solutions of each of the isolated sulfonates. Reaction mixture samples were typically diluted from 1:10 to 1:100 to ensure the sample concentration was within the calibrated range. Peaks for the positional isomers were summed to give a total component concentration. Solvent gradient profiles and approximate retention times are listed in Table 8.

carbonate/1.0 mM sodium bicarbonate in 18 mΩ water. The system was calibrated in the range of 0.05 to 5 ppm chloride and 0.1 to 10 ppm sulfate (diluted from 1000 ppm standard solutions of each supplied by Inorganic Ventures). Samples for analysis were diluted in 18 mΩ water to within the calibrated range (typically 1:10,000 to 1:100,000 dilutions). Under these conditions, chloride eluted at 4.5 minutes and sulfate eluted at 11.8 minutes. Alternatively to separate sulfite from sulfate, the mobile phase was changed to 3.0 mM potassium carbonate and 2.5 mM potassium bicarbonate. Under these conditions, chloride eluted at 4.9 minutes, sulfate eluted at 16.1 minutes, and sulfite eluted at 17.1 minutes. Standard samples of sulfite were prepared in 4 mM sodium hydroxide in 18 mΩ water to retard oxidation to sulfate, and were used immediately. Presence of sulfite in the standard solution was confirmed using QUANTOFIX™ Sulfite Test Sticks (available from Macherey-Nagel GmbH & Co., Düren, Germany, 10 to 1000 mg/L sulfite). Due to the facile oxidation of sulfite to sulfate under the analysis conditions, the IC system was not calibrated for determining sulfite concentrations.

Water concentrations were measured using a Mettler-Toledo DL31 Karl Fisher titrator (available from METTLER-TOLEDO INTERNATIONAL, INC.).

The present invention may be embodied in other forms without departing from the spirit and the essential attributes thereof, and, accordingly, reference should be made to the appended claims, rather than to the foregoing specification, as indicating the scope of the invention.

I claim:

1. A process comprising:
   contacting one or more Strecker sulfonation reaction products of one or more halogenated alkyl ethers in the presence of sulfite with one or more polar water soluble organic solvents selected from acetone, methyl ethyl ketone, and $C_2$-$C_5$ alkyl alcohols to form an extraction mixture;
   allowing the extraction mixture to separate into an aqueous phase and an organic phase;
   separating the aqueous phase from the organic phase;
   contacting the organic phase with a non-polar organic solvent selected from ethyl acetate, cyclohexane, toluene, alkyl ethers, hydrocarbons, and combinations thereof to form a mixed organic phase; and
   allowing the mixed organic phase time to separate cleanly into another aqueous phase and a final organic phase;
   wherein the one or more Strecker sulfonation reaction products each comprise at least 30 percent by weight of one or more inorganic salts on a dry basis and one or more surfactant components and the final organic phase following separation comprises less than 20 percent by weight on a dry basis of one or more inorganic salts.

2. The process of claim 1, wherein the one or more halogenated alkyl ethers comprise one or more alkyl ethers of 1,3-dichloro-2-propanol wherein the alkyl group is selected from the group of alkyls having eight or more carbon atoms.

3. The process of claim 1, wherein the $C_2$-$C_5$ alkyl alcohols are selected from 1-propanol, 2-propanol and 1-butanol.

4. The process of claim 1, wherein the one or more inorganic salts are selected from sodium sulfite, sodium bisulfate, sodium sulfate, sodium bisulfate, and sodium chloride, and their potassium counterparts.

5. The process of claim 1, wherein the one or more Strecker sulfonation reaction products each comprise between 40 and 60 percent by weight on a dry basis of the one or more inorganic salts.

6. The process of claim 1, wherein the extraction mixture comprises between 25 and 60 percent by weight on a dry basis of the one or more Strecker sulfonation reaction products.

7. The process of claim 1, wherein the final organic phase following separation comprises one or more surfactant components, the total amount of which is at least 75 percent of the amount of the one or more surfactant components of the one or more Strecker sulfonation products.

8. The process of claim 7, wherein the surfactant component of the final organic phase and the surfactant component of the one or more Strecker sulfonation products each comprise one or more disulfonated alkyl ethers, one or more monosulfonated alkyl ethers, or a combination thereof.

9. The process of claim 1, further comprising:
   distilling the final organic phase under a stream of inert gas to remove a portion of the one or more water soluble organic solvents there from and to obtain a concentrated surfactant solution.

10. The process of claim 9 wherein the concentrated surfactant solution comprises between 15 and 50 percent by weight of a surfactant component which comprises one or more disulfonated alkyl ethers, one or more monosulfonated alkyl ethers, or combinations thereof.

11. The process of claim 1, wherein the non-polar organic solvent is present in an amount between 20 and 60 percent by weight of the total weight of the one or more water soluble organic solvents.

12. The process of claim 1, further comprising:
    prior to contacting the one or more Strecker sulfonation reaction products with the one or more water soluble organic solvents, adding sufficient peroxide to the one or more Strecker sulfonation reaction products to oxidize sulfite to sulfate and achieve a positive peroxide test to form a peroxide-treated/sulfonate mixture;
    contacting the peroxide-treated/sulfonate mixture with ethyl acetate to form a peroxide-treated/sulfonate/ethyl acetate mixture;
    allowing the peroxide-treated/sulfonate/ethyl acetate mixture to separate into a water soluble surfactant phase comprising the one or more Strecker sulfonation reaction products wherein non-polar by-products have been removed there from.

13. The process of claim 1, wherein the aqueous phase comprises no greater than 1 percent by weight of one or more surfactant components.

14. The process of claim 1, wherein the one or more halogenated alkyl ethers comprises one or more dihalogenated alkyl ethers.

* * * * *